US00PP08634P

United States Patent [19]

Zary

[11] Patent Number: Plant 8,634

[45] Date of Patent: Mar. 8, 1994

[54] FLORIBUNDA ROSE PLANT NAMED 'JACANNE'

[75] Inventor: Keith W. Zary, Thousand Oaks, Calif.

[73] Assignee: Bear Creek Gardens, Inc., Medford, Oreg.

[21] Appl. No.: 990,742

[22] Filed: Dec. 15, 1992

[51] Int. Cl.[5] ..... A01H 5/00

[52] U.S. Cl. ..... Plt./28

[58] Field of Search ..... Plt. 28, 29

*Primary Examiner*—Howard J. Locker

*Attorney, Agent, or Firm*—Klarquist, Sparkman, Campbell, Leigh and Whinston

[57] ABSTRACT

A floribunda rose plant having powdery mildew resistance, few thorns, long vase life, vigorous, upright habit of growth, and the ability to flower in clusters of 3 to 5 flowers.

1 Drawing Sheet

The present invention relates to a new and distinct variety of rose plant of the floribunda class which was originated by me by crossing the variety POUlander U.S. Plant Pat. No. 6,265 with the variety AROprawn, U.S. Plant Pat. No. 5,397.

The primary objective of this breeding was to produce a new rose variety having the bright red flower color and vigor of the female variety coupled with the clustering ability of the male parent. The objective was substantially achieved along with other desirable improvements as evidenced by the following unique combination of characteristics which are outstanding in the new variety and which distinguish it from its parents, as well as from all other varieties of which I am aware:

1. Forms flowers in clusters of 3 to 5 roses;
2. Powdery mildew resistance;
3. Long vase life;
4. Vigorous, upright habit of growth; and
5. Very few thorns.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—POUlander U.S. Plant Pat. No. 6,265.

*Pollen parent.*—AROprawn, U.S. Plant Pat. No. 5,397.

Classification:

*Botanical.*—Rosa hybrida.

*Commercial.*—Floribunda.

FLOWER

Observations made from specimens grown in a greenhouse environment in Somis, Calif., from March through August, 1992.

Blooming habit: Recurrent.

Bud:

*Size.*—$\frac{3}{4}$ inch when the petals start to unfurl.

*Form.*—Short, blunt topped.

*Color.*—When sepals first divide, bud color is Red Group 44A. When half blown, the upper and lower sides of the petals are Red Group 44A.

*Sepals.*—Color: Green Group 138A. Surface texture: Covered in fine hairs. There are three lightly appendaged sepals. There are two unappendaged sepals with hairy edges.

*Receptacle.*—Color: Green Group 138A. Shape: Apple. Size: Large (5/16×5/16 inch). Surface: Smooth.

*Peduncle.*—Length: Medium (3 inches). Surface: Smooth, with occasional very fine glands. Color: Medium green. Strength: Stiff, erect.

Bloom:

*Size.*—Small. Average open size is $1\frac{3}{4}$ to 2 inches.

*Borne.*—Several together, in flat clusters.

*Stems.*—Medium (14 to 18 inches).

*Form.*—When first open: High center. Permanence: Retains its form to the end, outer petals curl back.

*Petalage.*—Number of petals under normal conditions: 35.

*Color.*—The upper and reverse sides of the petals are Red Group 44A. The bases of the petals have a distinctive white half moon ($\frac{1}{4}\times\frac{1}{4}$ inch) on the upper and lower sides. The major color on the upper side is Red Group 44A.

*Variegations.*—On each guard petal, there is a white streak down the center.

*Discoloration.*—No change in general tonality at the end of the first day or at the end of the third day.

*Fragrance.*—Slight.

Petals:

*Texture.*—Thick, leathery.

*Shape.*—Deltoid.

*Form.*—Tips slightly recurved.

*Arrangement.*—Imbricated, with no petaloids in the center.

*Persistence.*—Hang on and dry.

*Lastingness.*—On the plant: Very long (7 days). As a cut flower: Very long (9 to 10 days).

Reproductive parts:

*Anthers.*—Size: Medium. Quantity: Many. Color: Yellow. Arrangement: Regular around styles.

*Filaments.*—Color: White.

*Pollen.*—Color: Lemon yellow.

*Styles.*—Color: Reddish.

*Stigmas.*—Color: Greenish white.

Form: Bush.

Growth: Vigorous, upright, branching.

Foliage: Number of leaflets on normal midstem leaves: 5 or 7.

*Size.*—Medium (4×3 inches).

*Quantity.*—Abundant.

*Color.*—New foliage: Reddish. Old foliage: Dark green.

Leaflets:

*Shape.*—Broadly oval.

*Texture.*—Upper side: Leathery.

*Edge.*—Serrated.

*Serration.*—Single, small.

*Petiole rachis.*—Color: Green.

*Petiole underside.*—Smooth.

*Stipules.*—Long (½ inch), bearded.

*Disease resistance.*—Resistant to mildew under normal growing conditions at Somis, Calif.

Wood:

*New wood.*—Color: Light Green. Bark: Smooth.

*Old wood.*—Color: Green. Bark: Smooth.

Prickles:

*Quantity.*—On main canes from base and on laterals from main canes: Few.

*Form.*—Hooked downward (¼ inch long).

*Color when young.*—Green.

Small prickles:

*Quantity.*—On main stalks and on laterals: None.

I claim:

1. A new and distinct variety of rose plant of the floribunda class, substantially as herein shown and described, characterized particularly as to novelty by the unique combination of its powdery mildew resistance, few thorns, long vase life, vigorous, upright habit of growth, and its flowering in clusters of 3 to 5 flowers.

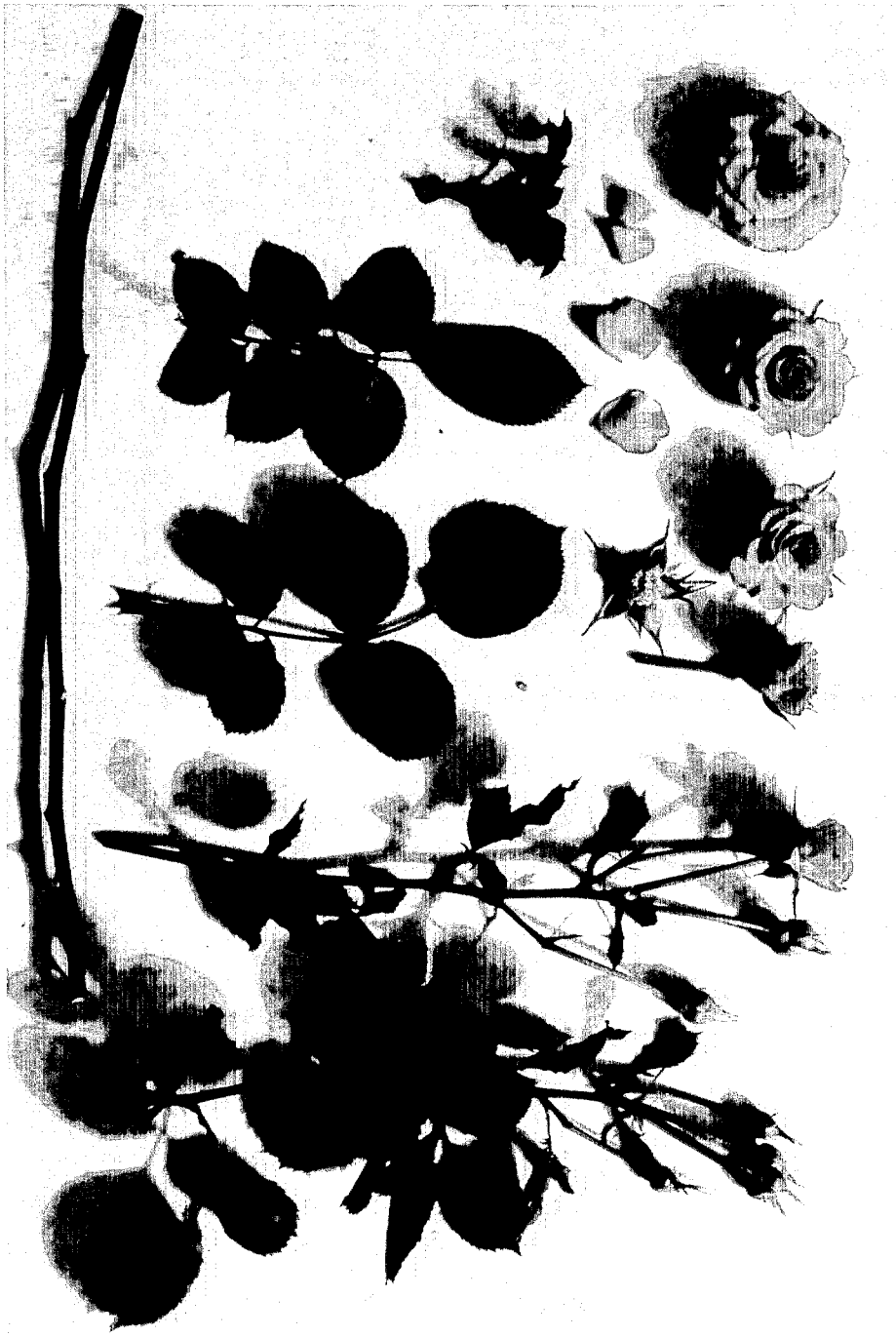

* * * * *